(12) United States Patent
Askham

(10) Patent No.: US 6,231,790 B1
(45) Date of Patent: May 15, 2001

(54) TETRAKIS-PENTAFLUOROPHENYL BORATES FROM PENTAFLUOROPHENYL GRIGNARD REAGENTS

(75) Inventor: Fredric Askham, Loveland, CO (US)

(73) Assignee: Boulder Scientific Company, Mead, CO (US)

(*) Notice: Subject to any disclaimer, the term of this patent is extended or adjusted under 35 U.S.C. 154(b) by 0 days.

(21) Appl. No.: 08/751,985

(22) Filed: Nov. 19, 1996

(51) Int. Cl.[7] .................................................. C07F 3/02
(52) U.S. Cl. .................. 260/665 G; 260/665 R; 528/4; 568/1; 568/6; 585/931
(58) Field of Search ................. 528/4; 568/6, 1; 260/665 R, 665 G; 585/931

(56) References Cited

U.S. PATENT DOCUMENTS

| | | | |
|---|---|---|---|
| 5,362,423 | * 11/1994 | Ikeda et al. | 260/665 R |
| 5,399,780 | * 3/1995 | Ikeda et al. | 568/6 |
| 5,420,355 | * 5/1995 | Ikeda et al. | 568/6 |
| 5,473,036 | * 12/1995 | Piotrowski et al. | 528/4 |

FOREIGN PATENT DOCUMENTS 1944928   12/1960   (GB) .

* cited by examiner

Primary Examiner—John M. Cooney, Jr.
(74) Attorney, Agent, or Firm—Edward S. Irons

(57) ABSTRACT

Pentafluorophenyl Grignard reagents are reacted with a boron trihalide in a non-ethereal solvent such as toluene to produce a tetrakis pentafluorophenyl borate magnesium halide.

7 Claims, No Drawings

TETRAKIS-PENTAFLUOROPHENYL BORATES FROM PENTAFLUOROPHENYL GRIGNARD REAGENTS

FIELD OF THE INVENTION

The invention relates to novel Grignard reagents for the production of tetrakis-pentafluorophenyl borate magnesium halides and to the conversion of such halides to different tetrakis-pentafluorophenyl salts having borate anions useful in metallocene olefin polymerization catalysts.

BACKGROUND OF THE INVENTION

Combinations of an activating cation and a weakly coordinating borate anion are used as components of metallocene olefin polymerization catalysts. Procedures for preparation of the borate anion portion of such combinations are described in the prior art. See European patent applications Nos. 505,972 and 505,997, Japanese published patent application No. 63-238057, and PCT International Application WO 94/00459.

Grignard reactions are conventionally conducted in an ether solvent. U.S. Pat. No. 5,473,036 describes the reaction of a fluorophenyl Grignard with a boron trihalide in an ether solvent to produce a magnesium halide salt of a tetrakis-fluorophenyl borate. The patent states: "The ether is needed to solubilize the Grignard reagent, fluorophenyl magnesium bromide" (Col. 2, 11. 1–2). The magnesium halide is converted by cation exchange to a different tetrakis-fluorophenyl borate salt to provide a borate anion useful in metallocene catalyst synthesis.

SUMMARY OF THE INVENTION

One aspect of this invention provides solutions of Grignard reagents in solvents which are not an ether, in particular, hydrocarbon solvents.

Pursuant to another aspect of the invention, a pentafluorophenyl magnesium halide is reacted with a boron trihalide in a solvent which is not an ether to produce a tetrakis-pentafluorophenyl magnesium halide. The magnesium halide may be converted by reaction with a suitable cation, such as substituted ammonium, trityl or onium cation, to a compound comprising a weakly coordinating borate anion and an activating cation.

DEFINITIONS

Ether—A compound having the formula ROR, Ar—O—Ar or R—O—Ar in which R is alkyl and Ar is aryl.

Non-ethereal solvent—A solvent which is not an ether.

Isolated, crystalline Grignard reagents are typically compounds coordinated with a Lewis base, usually the ether solvent in which the reagent is prepared. Such coordinated ethers are an integral part of the Grignard and do not function as solvents.

Similarly, ethers coordinated with boron halide, e.g., $BX_3.OEt_2$ in which X is a halide, do not function as solvents in the methodology of this invention. Although such boron trihalide ether complexes are useful as a matter of convenience in the laboratory practice of the invention, boron halides per se are to be used commercially.

Non-interfering solvent—A solvent which does not interfere with the reaction between a pentafluorophenyl Grignard reagent, e.g., pentafluorophenyl magnesium chloride or bromide, and a boron trihalide.

Grignard reagent—Any art recognized compound which functions as a Grignard reagent. For the purposes of this invention, Grignard reagents have the formula RMgX (excluding any coordinated Lewis base such as an ether) in which X is a halogen, preferably chlorine or bromine and R is a straight or branched chain acyclic or cyclic two to eight carbon atom aliphatic hydrocarbon or a two to eight carbon atom aromatic hydrocarbon group which may be substituted with, inter alia, a halogen. Representative aliphatic hydrocarbons include methyl, propyl, isopropyl, pentyl, isopentyl, hexyl, isohexyl, cyclohexyl and methyl cyclohexyl groups. Representative aromatic groups include phenyl, tolyl, xylenyl groups which may be halogen or otherwise substituted.

Preferred Grignard reagents for one embodiment of this invention are fluorophenyl, in particular, pentafluorophenyl magnesium halides. A particularly preferred Grignard reagent is pentafluorophenyl magnesium bromide.

DESCRIPTION OF THE PREFERRED EMBODIMENTS

An important aspect of this invention provides solutions of Grignard reagents in non-ethereal solvents. A first solution of the Grignard in an ether, usually ethyl ether, is prepared. A non-ethereal solvent, preferably a hydrocarbon solvent, is then added, and ether is removed to provide a second solution of the Grignard reagent in the non-ethereal solvent.

The relative proportions of the ethereal and non-ethereal solvents are chosen to maintain the Grignard reagent in solution not only in the mixed solvent but also in the non-ethereal solvent after the ether component of the mixed solvent is removed. In general, both of the ethereal and non-ethereal components may constitute 30% to 70% by volume of the initial solvent mixture.

The ether component of the solvent mixture may have the formula R—O—R', in which R and R' are the same or different two to five or more carbon atom alkyl groups. Diethyl ether is preferred. Dipropyl, disopropyl, dibutyl and disobutyl ether solvents are also appropriate.

The non-interfering, non-ethereal solvent component is preferably a five to eight carbon atom, acyclic or cyclic, aliphatic, or six to nine carbon atom aromatic hydrocarbon. Representative hydrocarbon solvents include normal or iso pentane, hexane, heptane, octane, cyclohexane, methyl cyclohexane, benzene, toluene and xylene.

A preferred embodiment provides a method for producing a solution in a hydrocarbon solvent, e.g., toluene, of the Grignard reagent $(C_6F_5)$ MgX in which X is a halogen, preferably chlorine or bromine.

Pursuant to that embodiment, a solution of pentafluorophenyl magnesium halide in a solvent mixture including an ether and a non-interfering, non-ethereal, preferably hydrocarbon, solvent is provided. The ether component of the solvent mixture is then removed to provide a solution of pentafluorophenyl magnesium halide Grignard in the non-ethereal solvent. The Grignard is then reacted with a boron trihalide to produce a tetrakis-pentafluorophenyl magnesium halide in solution in the non-ethereal solvent.

Typically, an ethyl ether solution of from about 0.5 to 2.0 molar in pentafluorophenyl magnesium bromide Grignard reagent is utilized in the first step of the method. The non-interfering, non-ethereal solvent is combined with the solution of the Grignard reagent in an amount sufficient to maintain the tris-pentafluorophenyl borate magnesium halide produced in subsequent steps in solution.

Preferably, the ether component of the original solvent mixture is removed under vacuum, e.g., about 30 Torr, until the pot temperature rises to from 20° C. to 40° C., preferably 30° C. Ether removal provides a non-ethereal solution of the Grignard. Boron trihalide, which for laboratory purposes, may be in the form of an ether complex, e.g., $BF_3.OEt_2$, is added, preferably by injection, to the non-ethereal solution of the Grignard. A spontaneous temperature rise to about 40°

C. to 60° C. typically occurs, whereupon external heat is applied and a reaction temperature of 50° C. to 100° C., preferably 85° C. to 90° C., is established and maintained for a time period, usually of one to four hours, appropriate to substantially complete the production of the desired tetrakis-pentafluorophenyl borate magnesium halide. In a typical reaction, this halide may comprise more than 95% of the fluorine containing reaction products.

The tetrakis borate reaction product may optionally be isolated and reacted with a salt, such as chloride, containing an appropriate cation, such as ammonium, trityl or onium, to provide by cation exchange a compound comprising a weakly coordinating borate and an activating cation useful in the preparation of metallocene olefin polymerization catalysts. Representative ammonium salts contain, as the cation portion, $R_3NH^+$, where R can be phenyl (Ph) which is either unsubstituted or substituted (e.g., with such alkyl groups as lower alkyl, namely, ethyl and/or ethyl). Such ammonium salts may be exemplified by triethyl ammonium chloride or phenyldimethyl ammonium chloride. The corresponding trityl salts have a cation of the formula $PH_3C^+$, whereas the onium salts can contain a cation of the formula $PH_2I^+$.

The route for forming the ammonium and onium-containing products involves the reaction of the intermediate in water with the selected salt to precipitate the desired combination of weakly coordinating boron-containing anion and activating cation. The route for forming the trityl-containing products uses a hydrocarbon solvent medium (e.g., toluene) in which the by product salt is insoluble but the borate anion-cation is soluble.

EXAMPLE I

Pentafluorophenyl magnesium bromide (250 ml, 1.025 M in $Et_2O$) and dry, deoxygenated toluene (500 ml) were combined in a 1 l. flask which had previously been purged with nitrogen. Diethyl ether was removed under vacuum (~30 Torr) until the pot temperature rose to 32° C. At this point, 3 ml of the solution was withdrawn by syringe and hydrolyzed by addition to 30% aqueous HCl at 0° C. in a closed test tube to insure that volatile materials are not lost.

Analysis by gas chromatography showed about a 1:3 ratio of $Et_2O:C_6F_5H$ which indicates a 1:3 ratio of $Et_2O:C_6F_5MgBr$ in solution before hydrolysis.

The solvent stripping was continued until an additional 100 ml of toluene had been removed. Another 3 ml aliquot was hydrolyzed and analyzed by gas chromatography as above with the same result (1:3 $Et_2O:C_6F_5H$). These results indicate that at this point, no free $Et_2O$ remained in solution (i.e., $Et_2O$ is no longer a component of the solvent system). All $Et_2O$ is tightly bound to the magnesium of the Grignard reagent.

$BF_3.OEt_2$ (7.0 ml) was then injected causing a spontaneous temperature rise to 50° C. External heat was applied and the reaction temperature was maintained at 85–90° C. for a time sufficient to drive the reaction to completion. After cooling to room temperature, an aliquot was withdrawn and analyzed by $^{19}F$ NMR. This showed tetrakis pentafluorophenyl borate magnesium bromide to comprise >95% of the fluorine containing products.

This magnesium salt, optionally after isolation, may be reacted in known manner by cation exchange to provide a compound having an anion useful in a metallocene catalyst. Use of pentafluorophenyl magnesium chloride yields a similar result.

EXAMPLE II

Example I is repeated with the exception that pentafluorophenyl magnesium bromide is added to a preformed mixture of ethyl ether and toluene containing about 30% to 70% toluene.

EXAMPLE III

Example I is repeated with the exception that methyl cyclohexane is substituted for toluene.

What is claimed is:
1. The method which comprises:

(i) reacting a boron trihalide with a solution in a solvent which contains no free ether of a pentafluorophenyl magnesium bromide or chloride
   wherein a tetrakis-pentafluorophenyl borate magnesium bromide or chloride is produced.

2. The claim 1 method further comprising:

(ii) isolating said tetrakis-pentafluorophenyl borate magnesium bromide or chloride produced in step (i), and (iii) subjecting said tetrakis-pentafluorophenyl borate magnesium bromide isolated in step (ii) to a cation exchange reaction to produce a tetrakis pentafluorophenyl borate which has an anion useful as a metallocene olefin polymerization catalyst component.

3. The claim 1 or claim 2 method in which said solvent is toluene.

4. The method which comprises (i) providing a first solution of $C_6F_5$ MgBr in ethyl ether;

(ii) adding toluene to provide a second solution of said $C_6F_5$ MgBr in a mixture of said ethyl ether and toluene;

(iii) removing the ether from said second solution wherein a third solution of $C_6F_5$ MgBr in toluene is formed; and (iv) optionally isolating said $C_6F_5$ MgBr from said third solution.

5. The claim 4 method which comprises (i) providing a first solution of $C_6F_5$ MgBr in ethyl ether;

(ii) adding toluene to provide a second solution of said $C_6F_5$ MgBr in a mixture of said ethyl ether and toluene;

(iii) removing the ether from said second solution wherein a third solution of $C_6F_5$ MgBr in toluene is formed; and (iv) reacting $BF_3$ with said $C_6F_5$ MgBr in said third solution to produce tetrakis $(C_6F_5)_4B$ MgBr; and (v) subjecting said tetrakis $(C_6F_5)_4B$ MgBr to a cation exchange reaction to produce a different tetrakis pentafluorophenyl borate salt which has an anion useful as a metallocene polymerization catalyst component.

6. The method which comprises:

(i) reacting a boron trihalide with a solution of a pentafluorophenyl magnesium bromide or chloride in solution in a solvent that contains no free ethyl ether
   wherein a tetrakis-pentafluorophenyl borate magnesium bromide or chloride is produced.

7. A method for preparing a toluene or methyl cyclohexane solution of a Grignard reagent which comprises:

(i) providing a first solution of said Grignard reagent ethyl ether;

(ii) adding toluene or methyl cyclohexane to said first solution to provide a second solution of said Grignard reagent in a solvent mixture of ethyl ether and toluene or methyl cyclohexane; and (iii) removing said ethyl ether from said step (ii) second solution,
   wherein a non-ethereal solution of said Grignard reagent in said toluene or methyl cyclohexane is produced.

* * * * *